United States Patent
Treacy et al.

(10) Patent No.: US 6,342,518 B1
(45) Date of Patent: Jan. 29, 2002

(54) SYNERGISTIC INSECTICIDAL COMPOSITIONS

(75) Inventors: Michael Frank Treacy, Newtown, PA (US); Raymond Frank Borysewicz, Hamilton Square, NJ (US); Paul E. Rensner, Yardley, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/521,988

(22) Filed: Mar. 9, 2000

Related U.S. Application Data

(60) Provisional application No. 60/124,228, filed on Mar. 12, 1999, and provisional application No. 60/158,202, filed on Oct. 7, 1999.

(51) Int. Cl.⁷ .......................... A01N 25/00; A61K 31/40
(52) U.S. Cl. ..................... 514/427; 514/426; 424/405
(58) Field of Search ................ 514/426, 427; 424/405

(56) References Cited

U.S. PATENT DOCUMENTS

| | | | |
|---|---|---|---|
| 4,663,341 A | 5/1987 | Jacobson | 514/403 |
| 5,010,098 A | 4/1991 | Brown et al. | 514/426 |
| 5,116,850 A | 5/1992 | Stevenson | 514/341 |
| 5,304,573 A | 4/1994 | Hino et al. | 514/522 |
| 5,324,837 A | 6/1994 | Renga et al. | 544/333 |
| 5,369,121 A | 11/1994 | Harrison et al. | 514/403 |
| 5,462,938 A | 10/1995 | Annus et al. | 514/229.8 |
| 5,492,925 A | 2/1996 | Addor et al. | 514/422 |
| 5,543,573 A | 8/1996 | Takagi et al. | 514/590 |
| 5,708,170 A | 1/1998 | Annis et al. | 544/212 |

FOREIGN PATENT DOCUMENTS

| | | |
|---|---|---|
| WO | WO 96/10560 | 11/1996 |
| WO | WO 98/23153 | 4/1998 |
| WO | WO 98/23154 | 6/1998 |
| WO | WO 98/25461 | 6/1998 |

OTHER PUBLICATIONS

Miller et al. (CA 114:223492, abstract of Brighton Crop Prot. Conf., ——Pest Dis. (1990), (1), 43–8).*

Gregory T. Payne, et al., Structure–Activity Relationships for the Action of Dihydropyrazole Insecticides on Mouse Brain Sodium Channels, Pesticide Biochemistry and Physiology, Aug. 1, 1998, vol. 60, No. 3.

Keith D. Wing, et al., A Novel Oxadiazine Insecticide Is Bioactivated in Lepidopteran Larvae, Archives of Insect Biochemistry and Physiology 37:91–103 (1998).

* cited by examiner

*Primary Examiner*—Sabiha Qazi
(74) *Attorney, Agent, or Firm*—Barbara V. Maurer

(57) ABSTRACT

The present invention provides a synergistic insecticidal composition comprising as essential active ingredients a neuronal sodium channel antagonist and an arylpyrrole insecticide.

Also provided are methods for synergistic insect control and crop protection.

15 Claims, No Drawings

SYNERGISTIC INSECTICIDAL COMPOSITIONS

This application claims priority from copending provisional application(s) Serial No. 60/124,228 filed on Mar. 12, 1999 and Serial No. 60/158,202 filed on Oct. 7, 1999.

BACKGROUND OF THE INVENTION

Although insecticidal agents and compositions have been developed to control insect pests such as agrohorticultural pests or hygienic pests, and in practice have been used as a single or a mixed agent, economically efficient and ecologically safe insect control compositions are still being sought. Insecticidal compositions which allow for reduced effective dosage rates, increased environmental safety and lower the incidence of insect resistance are highly desirable. The rotational application of insect control agents having different modes of action may be adopted for good pest management practice, however, this approach does not necessarily give satisfactory insect control. Combinations of insect control agents have been studied, however, a high synergistic action has not always been found. Obtaining an insecticidal composition which demonstrates no cross-resistance to existing insecticidal agents, no toxicity problems and little negative impact on the environment is extremely difficult.

Therefore, it is an object of this invention to provide a synergistic insecticidal composition which demonstrates a high controlling effect with concomittant reduced crop production cost and reduced environmental load.

It is another object of this invention to provide methods for synergistic insect control and enhanced crop protection.

SUMMARY OF THE INVENTION

The present invention provides a synergistic insecticidal composition comprising as essential active ingredients a synergistically effective amount of a neuronal sodium channel antagonist and an arylpyrrole insecticide.

The present invention also provides a method for synergistic insect control which comprises contacting said insect with a synergistically effective amount of a combination of a neuronal sodium channel antagonist and an arylpyrrole insecticide.

The present invention further provides a method for the enhanced protection of plants from infestation and attack by insects.

DETAILED DESCRIPTION OF THE INVENTION

When two or more substances in combination demonstrate unexpectedly high biological activity, for example, insecticidal activity, the resulting phenomenon may be referred to as synergism. The mechanism of synergism is not fully understood, and quite possibly may differ with different combinations. However, the term "synergism" as used in this application designates a cooperative action encountered in a combination of two or more biologically active components in which the combined activity of the two or more components exceeds the sum of the activity of each component alone.

Surprisingly, it has now been found that a composition which comprises a combination of a neuronal sodium channel antagonist and an arylpyrrole insecticide provides superior insect control at lower levels of the combined active agents than may be achieved when the neuronal sodium channel antagonist or the arylpyrrole insecticide is applied alone.

As used in this application, the term neuronal sodium channel antagonist designates a compound which is capable of preventing the ability of a neuron cell to transfer sodium ions across the cell membrane. A neuron cell thus affected is unable to fire, resulting in paralysis, and ultimately mortality, in the target host. Descriptions of neuronal sodium channel antagonists and their mode of action may be found in Pesticide Biochemistry and Physiology, 60: 177–185 or Archives of Insect Biochemistry and Physiology, 37: 91–103, both of which are hereby incorporated by reference.

Neuronal sodium channel antagonists include compounds such as those described in U.S. Pat. No. 5,543,573; U.S. Pat. No. 5,708,170; U.S. Pat. No. 5,324,837 and U.S. Pat. No. 5,462,938, among other publications. Exemplary of the neuronal sodium channel antagonist compounds useful in the composition of this invention are those compounds having the structural formula

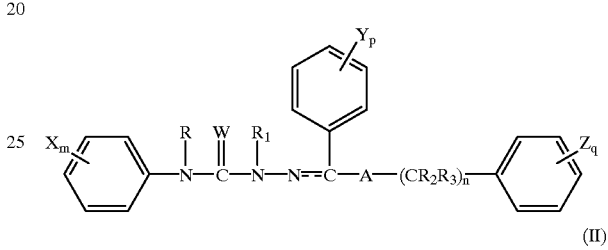

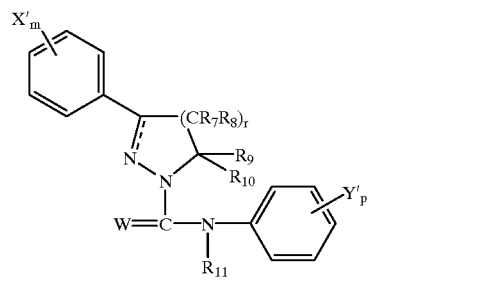

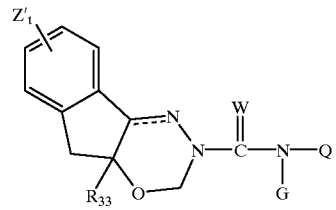

wherein
A is $CR_4R_5$ or $NR_6$;
W is O or S;
X, Y, Z, X', Y' and Z' are each independently H; halogen; OH; CN; $NO_2$; $C_1$–$C_6$alkyl optionally substituted with one or more halogen, $C_1$–$C_3$alkoxy, $C_1$–$C_3$haloalkoxy, $C_3$–$C_6$cycloalkyl, $C_2$–$C_6$alkenyloxy or sulfonyloxy groups;
$C_1$–$C_6$alkoxy optionally substituted with one or more halogen, $C_1$–$C_3$alkoxy or $C_3$–$C_6$cycloalkyl groups;
$C_1$–$C_6$alkoxycarbonyl, $C_3$–$C_6$cycloalkylcarbonyloxy, phenyl optionally substituted with one or more halogen, $C_1$–$C_4$alkyl, or $C_1$–$C_4$alkoxy groups;
aminocarbonyloxy optionally substituted with one or more $C_1$–$C_3$alkyl groups;
$C_1$–$C_6$alkoxycarbonyloxy; $C_1$–$C_6$alkylsulfonyloxy;
$C_2$–$C_6$alkenyl; or $NR_{12}R_{13}$;

m, p and q are each independently an integer of 1, 2, 3, 4, or 5;

n is an integer of 0, 1 or 2;

r is an integer of 1 or 2;

t is an integer of 1, 2, 3 or 4;

R, $R_1$, $R_2$, $R_3$, $R_4$ and $R_5$ are each independently H or $C_1$–$C_4$alkyl;

$R_6$ is H, $C_1$–$C_6$alkyl, $C_1$–$C_6$haloalkyl, $C_1$–$C_6$alkoxyalkyl, $C_1$–$C_6$alkoxy, $C_1$–$C_6$haloalkoxy, $C_2$–$C_6$alkenyl, $C_2$–$C_6$alkynyl, $C_1$–$C_6$alkylcarbonyl, $C_1$–$C_6$alkoxycarbonyl, $C_1$–$C_6$alkylthio, or $C_1$–$C_6$haloalkylthio;

$R_7$ and $R_8$ are each independently H; halogen; $C_1$–$C_6$alkyl; $C_1$–$C_6$alkylcarbonyloxy; or phenyl optionally substituted with one or more halogen, CN, $NO_2$, $C_1$–$C_6$alkyl, $C_2$–$C_6$haloalkyl, $C_1$–$C_6$alkoxy or $C_1$–$C_6$haloalkoxy groups;

$R_9$ and $R_{10}$ are each independently H, or $C_1$–$C_4$alkyl; $R_{11}$ is H, $C_1$–$C_6$alkyl, $C_1$–$C_6$haloalkyl, $C_1$–$C_4$alkylcarbonyl, $C_1$–$C_6$alkoxycarbonyl, or $C_1$–$C_6$haloalkoxycarbonyl;

$R_{12}$ and $R_{13}$ are each independently H or $C_1$–$C_6$alkyl;

G is H; $C_1$–$C_6$alkyl optionally substituted with one or more halogen, $C_1$–$C_4$alkoxy, $C_1$–$C_6$haloalkoxy, CN, $NO_2S(O)_uR_{14}$, $COR_{15}$, $CO_2R_{16}$, phenyl or $C_3$–$C_6$cycloalkyl groups;

$C_1$–$C_6$alkoxy; $C_1$–$C_6$haloalkoxy; CN; $NO_2$; $S(O)_uR_{17}$; $COR_{18}$; $CO_2R_{19}$; phenyl optionally substituted with one or more halogen, CN, $C_1$–$C_3$haloalkyl, or $C_1$–$C_3$haloalkoxy groups;

$C_3$–$C_6$cycloalkyl; or phenylthio;

Q is phenyl optionally substituted with one or more halogen, CN, SCN, $NO_2$, $S(O)_uR_{20}$, $C_1$–$C_4$alkyl, $C_1$–$C_4$haloalkyl, $C_1$–$C_4$alkoxyalkyl, $C_1$–$C_6$alkoxy, $C_1$–$C_6$haloalkoxy, or $NR_{21}R_{22}$ groups;

u is an integer of 0, 1 or 2;

$R_{14}$, $R_{15}$, $R_{16}$, $R_{18}$, $R_{19}$, $R_{21}$ and $R_{22}$ are each independently H or $C_1$–$C_6$alkyl;

$R_{17}$ and $R_{20}$ are each independently $C_1$–$C_6$alkyl or $C_1$–$C_6$haloalkyl;

$R_{33}$ is $CO_2R_{34}$;

$R_{34}$ is H, $C_1$–$C_6$alkyl, $C_1$–$C_6$haloalkyl, phenyl or halophenyl; and the dotted line configuration C===N represents a double bond or a single bond (i.e. C—N or C=N); or a stereoisomer thereof.

Preferred neuronal sodium channel antagonists suitable for use in the composition of the invention are those compounds of formula I, II or III wherein the dotted line configuration C===N represents a double bond.

More preferred neuronal sodium channel antagonists suitable for use in the inventive composition are those compounds of formula I or formula III wherein the dotted line configuration represents a double bond.

Particularly preferred neuronal sodium channel antagonists useful in the composition of the invention are those compounds of formula I or formula III wherein W is O; X is trifluoromethoxy and is in the 4-position; Y is trifluoromethyl and is in the 3-position; Z is CN and is in the 4-position; A is $CH_2$; n is 0; m, p and q are each 1; R and $R_1$ are each H; Z' is Cl; $R_{33}$ and G are each $CO_2CH_3$; Q is p-(trifluoromethoxy)phenyl; and the dotted line configuration C===N represents a double bond; or a stereoisomer thereof.

Further neuronal sodium channel antagonist compounds include those described in U.S. Pat. No. 5,116,850 and U.S. Pat. No. 5,304,573, among other publications. Exemplary of further neuronal sodium channel antagonist compounds suitable for use in the composition of the invention are those compounds having structural formula

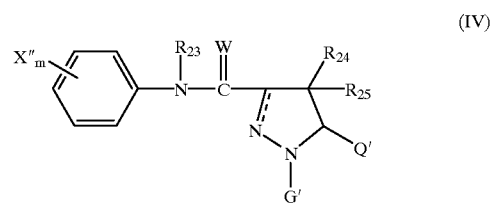

(IV)

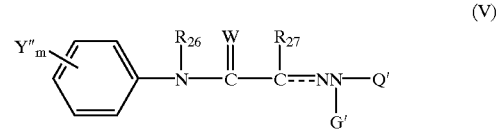

(V)

wherein

W is O or S;

X" and Y" are each independently H; halogen; CN; SCN; $C_1$–$C_6$alkyl optionally substituted with one or more halogen, $NO_2$, CN, $C_1C_4$alkoxy, $C_1$–$C_4$alkylthio, phenyl, halophenyl, $C_1$–$C_4$alkylsulfonyl, $C_1$–$C_4$haloalkylsulfonyl, or $C_1$–$C_4$alkoxycarbonyl groups;

$C_2$–$C_4$alkenyl; $C_2$–$C_4$haloalkenyl; $C_2$–$C_4$alkynyl; $C_2$–$C_4$haloalkynyl; $C_3$–$C_6$cycloalkyl; $C_3$–$C_6$halocycloalkyl; phenyl optionally substituted with one or more halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfonyl or $C_1$–$C_4$haloalkylsulfonyl groups;

$C_1$–$C_4$alkylcarbonyl; $C_1$–$C_4$haloalkylcarbonyl; or $NR_{28}R_{29}$;

m is an integer of 1, 2, 3, 4 or 5;

G' is phenyl optionally substituted with one or more groups which may be the same or different selected from X";

a 5-membered heteroaromatic ring containing one or two heteroatoms selected from 0 or 1 oxygen, 0 or 1 sulfur and 0, 1 or 2 nitrogen atoms said 5-membered heteroaromatic ring being attached via carbon and being optionally substituted with one or more groups which may be the same or different selected from X"; or a 6-membered heteroaromatic ring containing one or two heteroatoms selected from 0 or 1 oxygen, 0 or 1 sulfur and 0, 1 or 2 nitrogen atoms said 6-membered heteroaromatic ring being attached via carbon and being optionally substituted with one or more groups which may be the same or different selected from X";

Q' is H; $C_1$–$C_6$alkyl optionally substituted with one or more halogen, CN, $C_1$–$C_3$alkoxy, $C_1$–$C_6$alkoxycarbonyl, or phenyl optionally substituted with one or more halogen, CN, $NO_2$, $C_1$–$C_4$alkyl, $C_1$–$C_4$haloalkyl, $C_1$–$C_4$alkylsulfonyl or $C_1$–$C_4$alkylsulfinyl groups;

$C_2$–$C_6$alkenyl; $C_2$–$C_6$alkynyl; or phenyl optionally substituted with one to three groups, which may be the same or different, selected from X";

$R_{23}$, $R_{24}$, $R_{25}$, $R_{26}$, $R_{27}$, $R_{28}$ and $R_{29}$ are each independently H or $C_1$–$C_4$alkyl; and the dotted line configuration C===N represents a double bond or a single bond (i.e. C—N or C=N); or a stereoisomer thereof.

Further preferred neuronal sodium channel antagonist compounds of the invention are those compounds of formula IV or V wherein the dotted line configuration C═══N represents a double bond.

Other preferred neuronal sodium channel antagonist compounds suitable for use in the composition of the invention are those compounds of formula IV or V wherein W is O; X" and Y" are each independently H or $C_1$–$C_6$haloalkyl; m is 1; $R_{23}$, $R_{24}$, $R_{25}$, $R_{26}$ and $R_{27}$ are each H; G is phenyl optionally substituted with one or more halogen atoms; Q' is halophenyl or $C_1$–$C_4$alkyl optionally substituted with one phenyl or halophenyl group; and the dotted line configuration C═══N represents a double bond; or a stereoisomer thereof.

Arylpyrrole insecticides include those described in U.S. Pat. No. 5,010,098; U.S. Pat. No. 5,492,925; U.S. Pat. No. 5,484,807 and U.S. Pat. No. 5,284,863, among other publications. Exemplary of the arylpyrrole insecticides suitable for use in the composition of the invention are those arylpyrroles having the structural formula (VI)

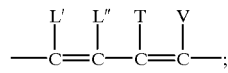

wherein
Ar is

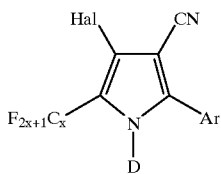

Hal is Cl or Br;
x is an integer of 1, 2, 3, 4, 5 or 6;
D is H; $C_1$–$C_6$alkyl optionally substituted with one or more halogen, CN, OH, $C_1$–$C_4$alkoxy, $C_1$–$C_4$haloalkoxy, $C_1$–$C_5$alkylthio, $C_1$–$C_4$alkylcarbonyloxy, $C_1$–$C_4$haloalkylthio, $C_2$–$C_6$alkenylcarbonyloxy, phenylcarbonyloxy, halophenylcarbonyloxy, phenoxy, halophenoxy, phenyl, halophenyl or $C_1$–$C_3$alkylphenyl groups, $C_2$–$C_6$alkenyl; $C_2$–$C_6$haloalkenyl; CN; $C_2$–$C_6$alkynyl; $C_2$–$C_6$haloalkynyl; di-($C_1$–$C_4$alkyl) aminocarbonyl; or $C_3$–$C_6$polymethyleneiminocarbonyl;
L is H or halogen;
M and $M^1$ are each independently H, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsufonyl, $C_1$–$C_4$haloalkylsulfonyl, $C_1$–$C_4$alkylcarbonyl, $C_1$–$C_4$haloalkylcarbonyl, $NR_{35}R_{36}$ or when M and $M^1$ are attached to adjacent carbon atoms, they may be taken together with the carbon atoms to which they are attached to form a ring in which $MM^1$ represents —$OCH_2O$—, —$OCF_2O$— or —CH═CH—CH═CH—;
A' is O or S;

$R_{30}$, $R_{31}$ and $R_{32}$ are each independently hydrogen, halogen, $NO_2$, CHO or $R_{31}$ and $R_{32}$ may be taken together with the carbon atoms to which they are attached to form a ring in which $R_{31}R_{32}$ represent

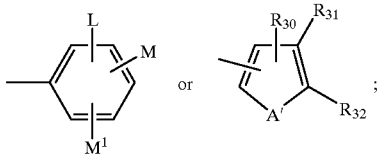

L', L", T and V are each independently H, halogen, CN or $NO_2$ with the proviso that no more than two of L', L", T or V are $NO_2$; and
$R_{35}$ and $R_{36}$ are each independently H or $C_1$–$C_4$alkyl.

Preferred arylpyrroles suitable for use as one essential active ingredient in the composition of the invention are those arylpyrroles of formula VI wherein D is H or ethoxymethyl; Ar is phenyl substituted with one or more halogen or halomethyl groups; and n is 1.

Preferred embodiments of the invention are those having a neuronal sodium channel antagonist compound of formula I or formula III and an arylpyrrole compound of formula VI as active ingredients.

More preferred embodiments of the invention are those having a formula I or formula III compound wherein W is O; X is trifluoromethoxy and is in the 4-position; Y is trifluoromethyl and is in the 3-position; Z is CN and is in the 4-position; A is $CH_3$; n is 0; m, p and q are each independently 1; R and $R_1$ are each independently H; Z' is Cl;, $R_{33}$ and G are each independently $CO_2CH_3$; Q is p-(trifluoromethoxy)phenyl; and the dotted line configuration C═══N represents a double bond and a formula VI arylpyrrole wherein D is H or ethoxymethyl; Ar is phenyl substituted with one or more halogen or halomethyl groups; and x is 1.

Particularly preferred embodiments of the invention are those having as the active ingredients a compound of formula I or III wherein W is O; X is trifluoromethoxy and is in the 4-position; Y is trifluoromethyl and is in the 3-position; Z is CN and is in the 4-position; A is $CH_3$; n is 0; m, p and q are each 1; R and $R_1$ are each H; Z' is Cl;, $R_{33}$ and G are each $CO_2CH_3$; and Q is p-(trifluoromethoxy) phenyl, and the dotted line configuration C═══N represents a double bond and an arylpyrrole of formula VI wherein D is H or ethoxymethyl; Ar is p-chlorophenyl or 3,5-dichlorophenyl; and x is 1.

In the specification and claims the term haloalkyl designates an alkyl group $C_xH_{2x+1}$ having 1 to 2x+1 halogen atoms which may be the same or different. Similarly, the terms haloalkenyl, haloalkynyl, haloalkoxy, halophenyl and the like designate mono- to perhalogen substitution wherein the halogens may be the same or different. Halogen designates Cl, Br, I or F.

Each of the compounds of formula I, II, III, IV and V embody assymetric centers which may be represented in the stereoisomeric R-form or S-form. The present invention also includes the R-form, the S-form or mixtures comprising the R-form and the S-form in any ratio. For compounds of formula III, the S-form is preferred.

Advantageously, the neuronal sodium-channel antagonist compound of formula I, II, III, IV or V or a mixture thereof may be formulated with an arylpyrrole insecticide. Said formulation may then be dispersed in a solid or liquid diluent for application to the insect, its food supply, breeding ground or habitat as a dilute spray or as a solid dust or dust concentrate. Customary formulation adjuvants as well as additional agriculturally acceptable active ingredients may be added and are within the scope of the invention.

The active ingredients of the inventive composition may also be formulated separately as a wettable powder, emulsifiable concentrate, aqueous or liquid flowable, suspension concentrate or any one of the conventional formulations used for insect control agents and tank mixed in the field with water or other inexpensive liquid for application as a liquid spray mixture. The separately formulated compositions may also be applied sequentially.

In actual practice, the composition of the invention is applied to the plant foliage or plant stem or insect habitat as a dilute spray prepared from any of the above-said formulations. In practice it has been found that the active ingredients of the composition of the invention are highly synergistic when present at a ratio of neuronal sodium channel antagonist compound to arylpyrrole insecticide of about 1:10 to 1:50.

The compositions of the invention are superior insecticidal compositions and are especially useful for protecting growing and harvested plants including: leguminous crops such as soybeans, snap beans, peas, wax beans and the like as well as cotton, forage crops, cole crops, leafy vegetables, tobacco, hops, tomatoes, potatoes, flowering ornamentals such as chrysanthemums, vine crops such as grapes, squash, pumpkin or melon and fruit trees such as cherry, peach, apple or citrus, from the ravages of insects.

The synergistic insecticidal composition of the invention is found to be highly active against a wide variety of lepidopteran and coleopteran insects such as *Helicoverpa zea* (cotton bollworm), *Heliothis virescens* (tobacco budworm), *Leptinotarsa decemlineata* (Colorado potato beetle), Diabrotica spp. (corn rootworm) and the like.

Further, the composition of the invention may be useful in the prevention and control of public health pests such as houseflies, mosquitoes, cockroaches, ants, termites or the like.

These and other advantages of the invention may become more apparent from the examples set forth herein below. These examples are provided merely as illustrations of the invention and are not intended to be construed as a limitation thereof.

EXAMPLE 1

Evaluation of the Synergistic Insecticidal Effect of a Combination of a Neuronal Sodium Channel Antagonist Plus an Arylpyrrole Insecticide In this evaluation, the *Heliothis zea* (cotton bollworm), *Heliothis virescens* (tobacco budworm) and pyrethroid-resistant *Heliothis virescens* larvae used are obtained from laboratory colonies. Pyrethroid-resistant *H. virescens* are derived from the PEG-strain [Campannola & Plapp, Proceedings of Beltwide Cotton Conference (1988)].

Cotton leaves are immersed in 1:1 v/v, acetone/water solutions of test compound, or solutions of a combination of test compounds for a period of about 3 seconds. Following immersion, leaves are allowed to air-dry for 2–3 hours. Plastic bioassay trays containing multiple open-faced wells (4.0×4.0×2.5 cm) are used as the test arenas. Cut portions of a treated leaf, a moistened cotton dental wick and a single third-instar larva are placed into each well, covered with an adhesive vented clear plastic sheet and held under constant fluorescent light at about 27° C. for a predetermined period of time. Larval mortality/morbidity is evaluated at 5 days after treatment. All treatments are replicated 4–5 fold in a randomized complete block design with 16–32 larvae per treatment. A log-probit analysis is applied to all data obtained. The results are summarized in Tables I, II and III hereinbelow.

TABLE I

Evaluation of the Synergistic Control of Cotton Bollworm

| Treatment | Dose (ppm) | % Larval Mortality | Toxicity Ratio[3,4] |
|---|---|---|---|
| A[1] | 0.816 | 0 | — |
| B[2] | 0.0816 | 9 | — |
| A + B | 0.816 + 0.0816 | 50 | 5.6 |
| A | 1.0 | 9.4 | — |
| B | 0.1 | 19.8 | — |
| A + B | 1.0 + 0.1 | 62.5 | 2.1 |

[1]A = formula VIa arylpyrrole
[2]B = formula Ia neuronal sodium channel antagonist
[3]Toxicity Ratio = % mortality (A + B) / (% mortality A + % mortality B)
[4]Toxicity Ratio > 1 = synergistic

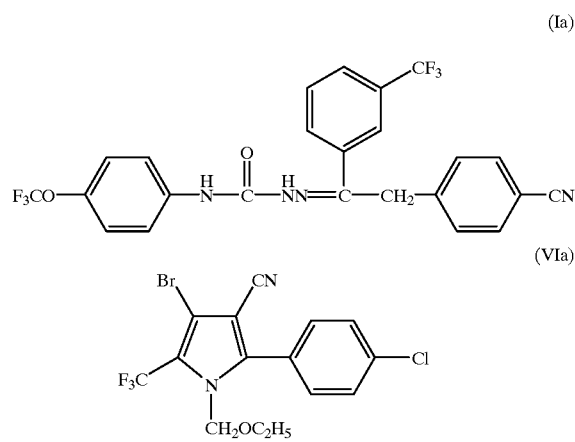

TABLE II

Evaluation of the Synergistic Control of Tobacco Budworm

| Treatment | Dose (ppm) | % Larval Mortality | Toxicity Ratio[3,4] |
|---|---|---|---|
| A[1] | 0.974 | 3 | — |
| B[2] | 0.0974 | 25 | — |
| A + B | 0.974 + 0.0974 | 50 | 1.8 |
| A | 1.0 | 10 | — |
| B | 0.1 | 30 | — |
| A + B | 1.0 + 0.1 | 51.3 | 1.28 |

[1]A = formula VIa arylpyrrole
[2]B = formula Ia neuronal sodium channel antagonist
[3]Toxicity Ratio = % mortality (A + B) / (% mortality A + % mortality B)
[4]Toxicity Ratio > 1 = synergistic

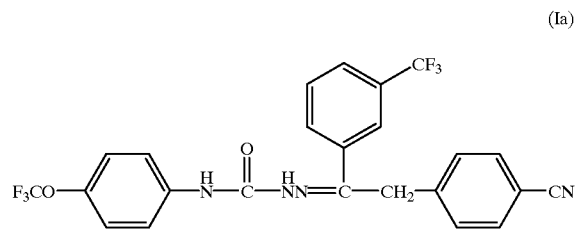

-continued (VIa)

[Chemical structure: pyrrole with Br, CN, F₃C, Cl-phenyl, CH₂OC₂H₅ substituents]

TABLE III

Evaluation of the Synergistic Control of Pyrethroid-Resistant Tobacco Budworm

| Treatment | Dose (ppm) | % Larval Mortality | Toxicity Ratio[3,4] |
|---|---|---|---|
| A[1] | 0.997 | 0 | — |
| B[2] | 0.0997 | 29 | — |
| A + B | 0.997 + 0.0997 | 50 | 1.7 |
| A | 2.093 | 7 | — |
| B | 0.0419 | 8 | — |
| A + B | 2.093 + 0.0419 | 50 | 3.3 |
| A | 1.0 | 6.2 | — |
| B | 0.1 | 25.0 | — |
| A + B | 1.0 + 0.1 | 56.3 | 1.8 |
| A | 3.0 | 34.4 | — |
| B | 0.06 | 14.1 | — |
| A + B | 3.0 + 0.06 | 81.2 | 1.67 |

[1]A = formula VIa arylpyrrole
[2]B = formula Ia neuronal sodium channel antagonist
[3]Toxicity Ratio = $\frac{\% \text{ mortality (A + B)}}{\% \text{ mortality A} + \% \text{ mortality B}}$
[4]Toxicity Ratio > 1 = synergistic (Ia)

[Chemical structure of formula Ia]

(VIa)

[Chemical structure of formula VIa]

What is claimed is:

1. A synergistic insecticidal composition comprising a synergistically effective amount of a neuronal sodium channel antagonist compound of the formula (I)

[Chemical structure of formula I]

wherein
A is $CR_4R_5$ or $NR_6$;
W is O or S;
X, Y, and Z, are each independently H; halogen; OH; CN; $NO_2$;
$C_1$–$C_6$alkyl optionally substituted with one or more halogen, $C_1$–$C_3$alkoxy, $C_1$–$C_3$haloalkoxy, $C_3$–$C_6$cycloalkyl, $C_2$–$C_6$alkenyloxy or sulfonyloxy groups;
$C_1$–$C_6$alkoxy optionally substituted with one or more halogen, $C_1$–$C_3$alkoxy or $C_3$–$C_6$cycloalkyl groups;
$C_1$–$C_6$alkoxycarbonyl, $C_3$–$C_6$cycloalkylcarbonyloxy, phenyl optionally substituted with one or more halogen, $C_1$–$C_4$alkyl, or $C_1$–$C_4$alkoxy groups;
aminocarbonyloxy optionally substituted with one or more $C_1$–$C_3$alkyl groups;
$C_1$–$C_6$alkoxycarbonyloxy; $C_1$–$C_6$alkylsulfonyloxy; $C_2$–$C_6$alkenyl; or $NR_{12}R_{13}$;
m, p and q are each independently an integer of 1, 2, 3, 4, or 5;
n is an integer of 0, 1 or 2;
R, $R_1$, $R_2$, $R_3$, $R_4$ and $R_5$ are each independently H or $C_1$–$C_4$alkyl;
$R_6$ is H, $C_1$–$C_6$alkyl, $C_1$–$C_6$haloalkyl, $C_1$–$C_6$alkoxyalkyl, $C_1$–$C_6$alkoxy, $C_1$–$C_6$haloalkoxy, $C_2$–$C_6$alkenyl, $C_2$–$C_6$alkynyl, $C_1$–$C_6$alkylcarbonyl, $C_1$–$C_6$alkoxycarbonyl, $C_1$–$C_6$alkylthio, or $C_1$–$C_6$haloalkylthio;
$R_{12}$ and $R_{13}$ are each independently H or $C_1$–$C_6$alkyl; and
the dotted line configuration C===N represents a double bond or a single bond; or
a stereoisomer thereof
and an arylpyrrole insecticide of formula VI (VI)

[Chemical structure of formula VI with Hal, CN, $F_{2x+1}C_x$, Ar, D substituents]

wherein
Ar is

[Chemical structure with L, M, $M^1$ substituents]

Hal is Cl or Br;
x is an integer of 1, 2, 3, 4, 5 or 6;
D is H, $C_1$–$C_6$alkyl optionally substituted with one or more halogen, CN, OH, $C_1$–$C_4$alkoxy, $C_1$–$C_4$haloalkoxy, $C_1$–$C_5$alkylthio, $C_1$–$C_4$alkylcarbonyloxy, $C_1$–$C_4$haloalkylthio, $C_2$–$C_6$alkenylcarbonyloxy, phenylcarbonyloxy, halophenylcarbonyloxy, phenoxy, halophenoxy, phenyl, halophenyl or $C_1$–$C_3$alkylphenyl groups,
$C_2$–$C_6$alkenyl, $C_2$–$C_6$haloalkenyl, CN, $C_2$–$C_6$alkynyl, $C_2$–$C_6$haloalkynyl, di-($C_1$–$C_4$alkyl)aminocarbonyl or $C_3$–$C_6$polymethyleneiminocarbonyl;

L is H or halogen;

M and $M^1$ are each independently H, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsufonyl, $C_1$–$C_4$haloalkylsulfonyl, $C_1$–$C_4$alkylcarbonyl, $C_1$–$C_4$haloalkylcarbonyl, $NR_{35}R_{36}$ or when M and $M^1$ are attached to adjacent carbon atoms, they may be taken together with the carbon atoms to which they are attached to form a ring in which $MM^1$ represents —$OCH_2O$—, —$OCF_2O$— or —CH=CH—CH=CH—; and $R_{35}$ and $R_{36}$ are each independently H or $C_1$–$C_4$alkyl.

2. The composition of claim 1 wherein the ratio of the neuronal sodium channel antagonist to the arylpyrrole insecticide is about 1:10 to 1:50.

3. The composition of claim 1, wherein the neuronal sodium channel antagonist and the arylpyrrole insecticide are dispersed in an inert solid or liquid diluent.

4. The composition of claim 1 wherein the dotted line configuration C===N represents a double bond.

5. The composition of claim 4 wherein W is O; X is trifluoromethoxy and is in the 4-position; Y is trifluoromethyl and is in the 3-position; Z is CN and is in the 4-position; A is $CH_2$; n is 0; m, p and q are each independently 1; R and $R_1$ are each independently H; D is H or ethoxymethyl; Ar is phenyl substituted with one or two halogen or halomethyl groups; and x is 1.

6. The composition of claim 5 wherein Hal is Br; Ar is 4-chlorophenyl, D is ethoxymethyl and $F_{2x=1}C_x$ is trifluoromethyl.

7. A method for synergistic insect control which comprises contacting said insect with a synergistically effective amount of a combination of a neuronal sodium channel antagonist compound of the formula

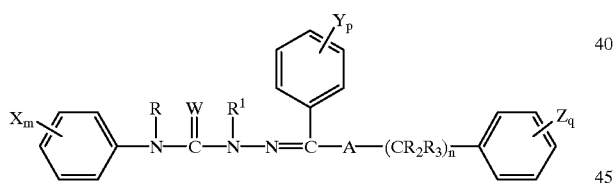

(I)

wherein

A is $CR_4R_5$ or $NR_6$;

W is O or S;

X, Y, and Z, are each independently H; halogen; OH; CN; $NO_2$;

$C_1$–$C_6$alkyl optionally substituted with one or more halogen, $C_1$–$C_3$alkoxy, $C_1$–$C_3$haloalkoxy, $C_3$–$C_6$cycloalkyl, $C_2$–$C_6$alkenyloxy or sulfonyloxy groups;

$C_1$–$C_6$alkoxy optionally substituted with one or more halogen, $C_1$–$C_3$alkoxy or $C_3$–$C_6$cycloalkyl groups;

$C_1$–$C_6$alkoxycarbonyl, $C_3$–$C_6$cycloalkylcarbonyloxy, phenyl optionally substituted with one or more halogen, $C_1$–$C_4$alkyl, or $C_1$–$C_4$alkoxy groups;

aminocarbonyloxy optionally substituted with one or more $C_1$–$C_3$alkyl groups;

$C_1$–$C_6$alkoxycarbonyloxy; $C_1$–$C_6$alkylsulfonyloxy; $C_2$–$C_6$alkenyl; or $NR_{12}R_{13}$;

m, p and q are each independently an integer of 1, 2, 3, 4, or 5;

n is an integer of 0, 1 or 2;

R, $R_1$, $R_2$, $R_3$, $R_4$ and $R_5$ are each independently H or $C_1$–$C_4$alkyl;

$R_6$ is H, $C_1$–$C_6$alkyl, $C_1$–$C_6$haloalkyl, $C_1$–$C_6$alkoxyalkyl, $C_1$–$C_6$alkoxy, $C_1$–$C_6$haloalkoxy, $C_2$–$C_6$alkenyl, $C_2$–$C_6$alkynyl, $C_1$–$C_6$alkylcarbonyl, $C_1$–$C_6$alkoxycarbonyl, $C_1$–$C_6$alkylthio, or $C_1$–$C_6$haloalkylthio;

$R_{12}$ and $R_{13}$ are each independently H or $C_1$–$C_6$alkyl; and the dotted line configuration C===N represents a double bond or a single bond; or a stereoisomer thereof and an arylpyrrole insecticide of formula VI

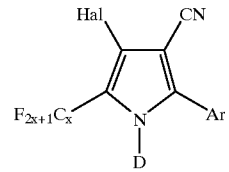

(VI)

wherein

Ar is

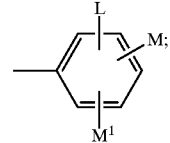

Hal is Cl or Br;

x is an integer of 1, 2, 3, 4, 5 or 6;

D is H, $C_1$–$C_6$alkyl optionally substituted with one or more halogen, CN, OH, $C_1$–$C_4$alkoxy, $C_1$–$C_4$haloalkoxy, $C_1$–$C_5$alkylthio, $C_1$–$C_4$alkylcarbonyloxy, $C_1$–$C_4$haloalkylthio, $C_2$–$C_6$alkenylcarbonyloxy, phenylcarbonyloxy, halophenylcarbonyloxy, phenoxy, halophenoxy, phenyl, halophenyl or $C_1$–$C_3$alkylphenyl groups, $C_2$–$C_6$alkenyl, $C_2$–$C_6$haloalkenyl, CN, $C_2$–$C_6$alkynyl, $C_2$–$C_6$haloalkynyl, di-($C_1$–$C_4$alkyl)aminocarbonyl or $C_3$–$C_6$polymethyleneiminocarbonyl;

L is H or halogen;

M and $M^1$ are each independently H, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsufonyl, $C_1$–$C_4$haloalkylsulfonyl, $C_1$–$C_4$alkylcarbonyl, $C_1$–$C_4$haloalkylcarbonyl, $NR_{35}R_{36}$ or when M and $M^1$ are attached to adjacent carbon atoms, they may be taken together with the carbon atoms to which they are attached to form a ring in which $MM^1$ represents —$OCH_2O$—, —$OCF_2O$— or —CH=CH—CH=CH—; and $R_{35}$ and $R_{36}$ are each independently H or $C_1$–$C_4$alkyl.

8. The method of claim 7 wherein the ratio of the neuronal sodium channel antagonist to the arylpyrrole insecticide is about 1:10 to 1:50.

9. The method of claim 7 wherein the neuronal sodium channel antagonist and the arylpyrrole insecticide are dispersed in an inert solid or liquid diluent.

10. The method of claim 7 wherein the dotted line configuration C===N represents a double bond.

11. The method of claim 10 wherein W is O; X is trifluoromethoxy and is in the 4-position; Y is trifluoromethyl and is in the 3-position; Z is CN and is in the 4-position; A is $CH_2$; n is 0; m, p and q are each independently 1; R and $R_1$ are each independently H; D is H or ethoxymethyl; Ar is phenyl substituted with one or two halogen or halomethyl groups; and x is 1.

12. The method of claim 11 wherein Hal is Br; Ar is 4-chlorophenyl, D is ethoxymethyl and $F_{2x-1}C_x$ is trifluoromethyl.

13. A method for protecting a plant from infestation and attack by insects which comprises applying to the foliage or stem of said plant a synergistically effective amount of a composition of claim 1.

14. The method of claim 13 wherein the plant is cotton.

15. The method of claim 13 wherein the insect is lepidoptera or coleoptera.

* * * * *